(12) United States Patent
Koslow

(10) Patent No.: US 7,276,166 B2
(45) Date of Patent: *Oct. 2, 2007

(54) FIBER-FIBER COMPOSITES

(75) Inventor: Evan E. Koslow, Weston, CT (US)

(73) Assignee: KX Industries, LP, Orange, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/923,058

(22) Filed: Aug. 19, 2004

(65) Prior Publication Data

US 2005/0051487 A1 Mar. 10, 2005

Related U.S. Application Data

(63) Continuation-in-part of application No. 10/286,695, filed on Nov. 1, 2002, now Pat. No. 6,835,311.

(60) Provisional application No. 60/518,266, filed on Nov. 7, 2003.

(51) Int. Cl.
*B01D 29/00* (2006.01)
*B01D 39/00* (2006.01)
*B01D 61/00* (2006.01)
*B01D 63/00* (2006.01)

(52) U.S. Cl. ............. 210/650; 210/490; 210/508; 210/502.1; 55/524

(58) Field of Classification Search ........ 210/505–508, 210/257.2, 195.1, 502.1, 668, 315, 767, 650, 210/490; 55/524; 428/304.5, 307.3, 311.11, 428/311.71
See application file for complete search history.

(56) References Cited

U.S. PATENT DOCUMENTS

| | | | | |
|---|---|---|---|---|
| 4,859,386 A | * | 8/1989 | VanderBilt et al. | 264/113 |
| 5,019,311 A | * | 5/1991 | Koslow | 264/122 |
| 5,393,601 A | * | 2/1995 | Heinrich et al. | 442/411 |
| 5,577,494 A | * | 11/1996 | Kuypers et al. | 128/201.13 |
| 5,681,468 A | * | 10/1997 | Sawan et al. | 210/500.25 |
| 5,681,469 A | * | 10/1997 | Barboza et al. | 210/503 |
| 5,828,430 A | * | 10/1998 | Nishida | 349/44 |
| 5,942,323 A | * | 8/1999 | England | 428/323 |
| 6,037,079 A | * | 3/2000 | Tanaka et al. | 429/142 |
| 6,267,898 B1 | * | 7/2001 | Fukuda et al. | 210/767 |
| 6,352,947 B1 | * | 3/2002 | Haley et al. | 442/364 |
| 6,387,415 B1 | * | 5/2002 | Garris | 424/618 |
| 6,579,906 B2 | * | 6/2003 | Cooper et al. | 514/646 |
| 6,630,016 B2 | * | 10/2003 | Koslow | 95/285 |
| 6,638,431 B2 | * | 10/2003 | Back et al. | 210/698 |
| 6,835,311 B2 | * | 12/2004 | Koslow | 210/490 |
| 6,866,704 B2 | * | 3/2005 | Koslow | 96/226 |
| 6,913,154 B2 | * | 7/2005 | Koslow | 210/489 |
| 6,949,820 B2 | * | 9/2005 | Reiss et al. | 257/698 |
| 6,953,604 B2 | * | 10/2005 | Koslow | 427/244 |
| 6,998,058 B2 | * | 2/2006 | Koslow | 210/764 |
| 7,008,537 B2 | * | 3/2006 | Koslow | 210/257.2 |
| 7,011,753 B2 | * | 3/2006 | Koslow | 210/263 |

* cited by examiner

*Primary Examiner*—Ana M. Fortuna
(74) *Attorney, Agent, or Firm*—DeLio & Peterson, LLC

(57) ABSTRACT

A fiber-fiber composite is disclosed herein comprising majority fibers and minority fibers, the minority fibers having a softening point lower than said majority fibers such that when the admixture of majority fibers and minority fibers are wet laid to form a paper-like structure and subjected to a pressure and a temperature above the softening point of said minority fibers, said majority fibers and minority fibers form said composite having a mean pore diameter equal to or less than about 1 μm with a porosity of greater than about 35%, and a wet strength of greater than about 0.013 kg/mm.

31 Claims, 4 Drawing Sheets

FIBER-FIBER COMPOSITES

This application claims priority from U.S. Provisional Application No. 60/518,266, filed on 7 Nov. 2003, and is a continuation-in-part of U.S. application Ser. No. 10/286,695 filed on 1 Nov. 2002, now U.S. Pat No. 6,835,311 the entirety of which are both hereby incorporated by reference.

The present invention is directed to a composite comprising of at least two types of fibers, preferably nanofibers, wherein one type of fiber binds the other fibers forming a fiber-fiber composite structure having a mean pore diameter of less than about 1 μm.

SUMMARY OF THE INVENTION

The present invention is directed to a composite flat sheet medium comprising of: majority fibers; and minority fibers admixed with the majority fibers wherein the minority fibers have a softening point lower than the majority fibers such that when the admixture of majority fibers and minority fibers are wet laid to form a paper-like structure and subjected to a pressure and a temperature above the softening point of the minority fibers, the majority fibers and minority fibers form the composite having a mean pore diameter equal to or less than about 1 μm with a porosity of greater than about 35%, and a wet strength of greater than about 0.013 kg/mm.

Preferably, the majority fibers or the minority fibers comprise of nanofibers, wherein the nanofibers comprise of glass, polymer, lyocell, cellulose, metal, ceramic, mineral, or combinations thereof. Preferably, the majority fibers comprise glass, polymer, lyocell, cellulose, metal, ceramic, mineral, or combinations thereof. Preferably, the minority fibers comprise a thermoset or thermoplastic polymer. For example, the minority fibers may comprise a polyolefin, polyvinyl alcohol, an acrylic, or combinations thereof. Preferably, the softening point of the minority fibers is at least 25° C. lower than a softening point of the majority fibers.

The composite of the present invention may have a mean pore diameter of the composite equal to or less than about 0.75 μm; a bubble point that is equal to or less than about 8 μm.

The composite of the present invention may further include a microbiological interception enhancing agent.

In another aspect, the present invention is directed to a filtration system comprising of: an activated carbon filter medium, in combination with a high wet strength nanofiber composite having a mean pore diameter of less than about 1 μm, wherein the nanofiber composite comprises of majority fibers; and minority fibers admixed with the majority fibers wherein the minority fibers have a softening point lower than the majority fibers such that when the admixture of majority fibers and minority fibers are subjected to pressure and a temperature above the softening point of the minority fibers, the majority fibers are coalesced into the high wet strength composite.

Preferably, the activated carbon filter medium comprises a carbon block having a mean pore diameter of greater than about 1 μm and wherein the filtration system can remove protozoan cysts. Alternatively, the activated carbon filter medium may comprise a flat sheet filter medium having immobilized therein activated carbon particles, alone or in combination with other active agents, between one or more substrates, or admixed with fibers to result in entanglement or bonds with the fibers within the activated carbon filter medium. Preferably, the nanofiber composite is the one or more substrates of the flat sheet filter medium. Also, the activated carbon filter medium may be formed into a spiral wound or pleated flat sheet filter element. The filtration system may further include a particulate prefilter.

Preferably, the nanofiber composite can be a prefilter placed upstream of the activated carbon filter medium. Either or both of the activated carbon filter medium and the nanofiber composite may further include a microbiological interception enhancing agent.

In yet another aspect, the present invention is directed to a method of removing microbiological contaminants from a contaminated liquid comprising the steps of: providing a filter medium comprising a fiber-fiber composite having a mean pore diameter equal to or less than about 1 μm, the composite formed from a wet laid admixture of majority fibers and minority fibers, wherein the minority fibers have a softening point lower than the majority fibers such that when the admixture of majority fibers and minority fibers are subjected to a pressure and a temperature above the softening point of the minority fibers, the majority fibers and minority fibers form a paper-like structure with a porosity of greater than about 40%; contacting the contaminated liquid with the composite; and removing 99.95% of contaminants having an average particle size greater than about 3 to about 5 μm.

The fiber-fiber composite may be a prefilter for the filter medium in a flat sheet, spiral wound or pleated configuration.

Preferably, in the step of providing a filter medium, the filter medium further includes an activated carbon filter medium. The activated carbon filter medium may comprise an activated carbon block, and wherein the fiber-fiber composite is wrapped around the activated carbon block, spiral wound and inserted within a core of the activated carbon block. The activated carbon filter medium may comprise a flat sheet medium comprising activated carbon particles immobilized on a substrate. Preferably, the fiber-fiber composite is a substrate of the flat sheet medium. A particulate prefilter may be added upstream from the activated carbon filter medium. The filter medium and/or the fiber-fiber composite can be treated with a microbiological interception enhancing agent.

BRIEF DESCRIPTION OF THE DRAWINGS

The features of the invention believed to be novel and the elements characteristics of the invention are set forth with particularity in the appended claims. The figures are for illustration purposes only and are not drawn to scale. The invention itself, however, both as to organization and method of operation, may be best understood by reference to the description of the preferred embodiment(s) that follows taken in conjunction with the accompanying drawings in that:

DETAILED DESCRIPTION OF THE PREFERRED EMBODIMENT(S)

Figure 1:
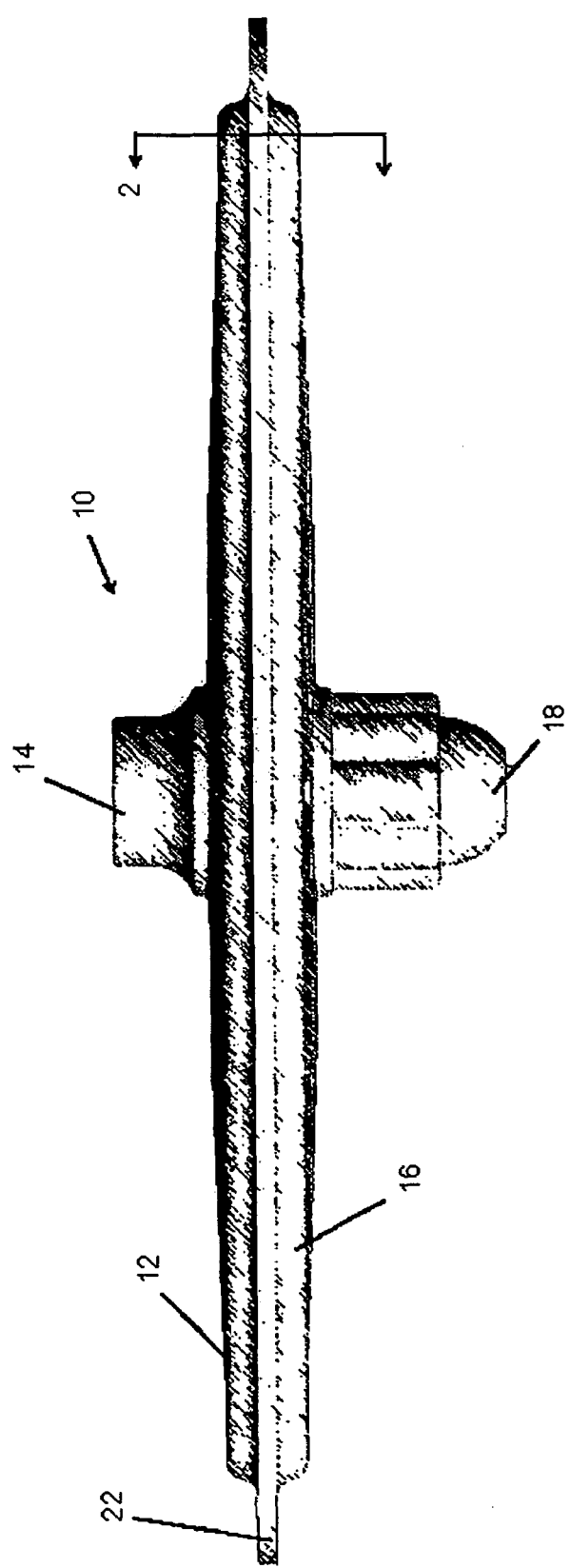
FIG. 1 is a side plan view of a filter incorporating the filter media of the present invention.
Figure 2:
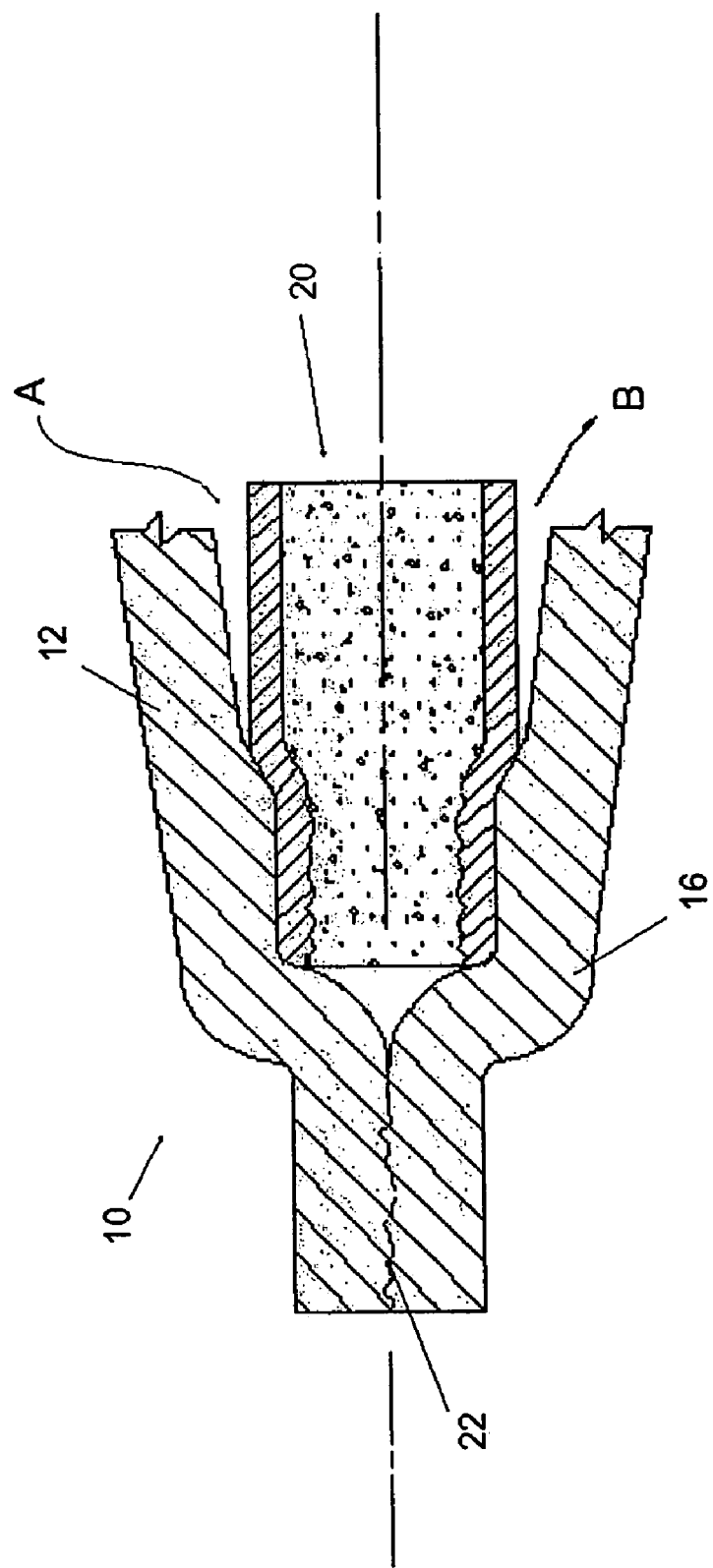
FIG. 2 is a cross sectional view of the filter of FIG. 1 taken at lines 2-2.
Figure 3:
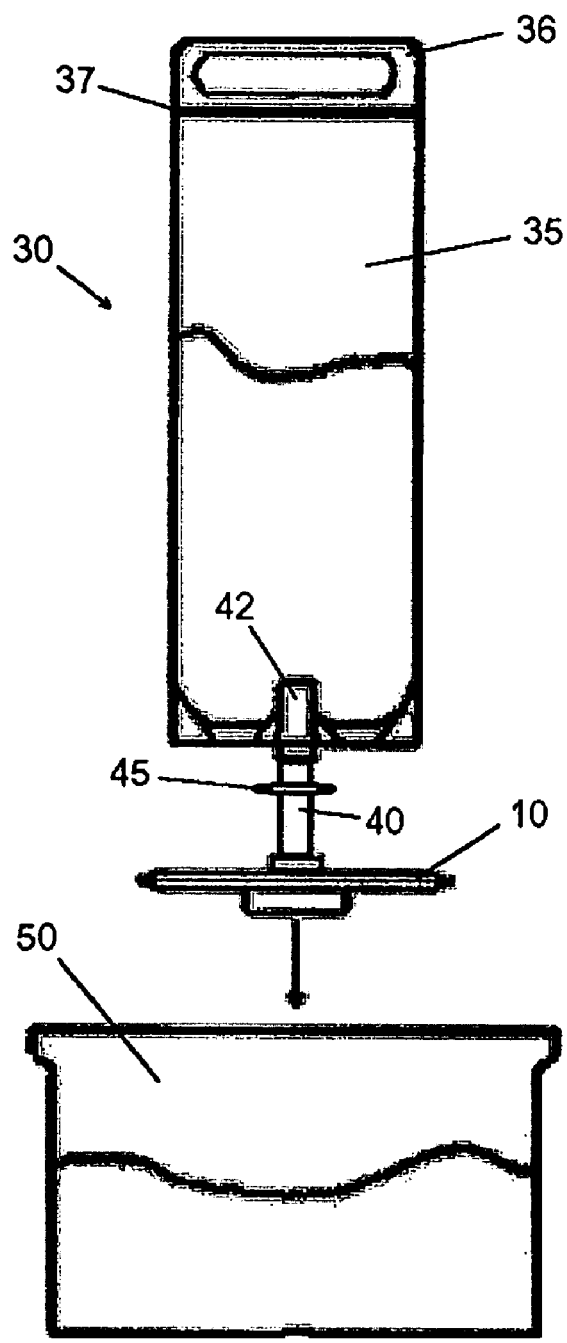
FIG. 3 is a front plan view of a filtration system of the present invention.
Figure 4:
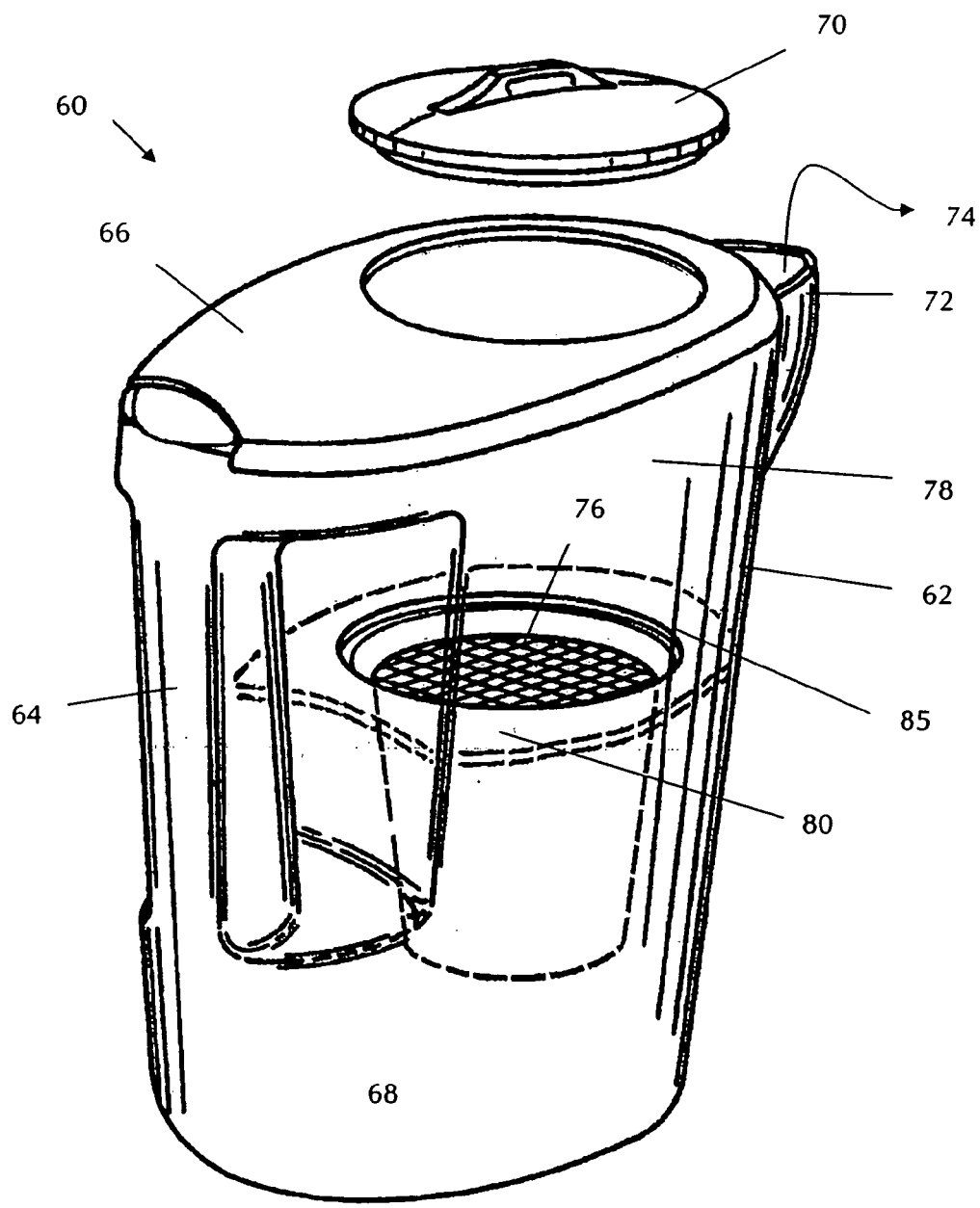
FIG. 4 is a perspective view of another filtration system of the present invention.

In describing the preferred embodiment of the present invention, reference will be made herein to FIGS. 1 to 4 of the drawings in that like numerals refer to like features of the invention. Features of the invention are not necessarily shown to scale in the drawings.

The fiber-fiber composite of the present invention includes majority fibers and minority fibers, wherein the majority fibers are present in an amount greater than the minority fibers. The minority fibers are present as a binder to provide an adhesive force coalescing the majority fibers into the composite structure when the minority fibers are heated to at least their softening point up to and including their melting point. The fiber-fiber composite of the present invention is useful as a filter medium alone and in combination with traditional filter media such as, for example, activated carbon filter media. The tight pore structure of the fiber-fiber composite of the present invention provides short diffusion distances from a fluid to the surface of the composite by adsorption or diffusive interception making it an excellent medium for fluid filtration. Pre- or post-treatment of the fiber-fiber composite can impart properties such as, for example, hydrophilicity, hydrophobicity, anti-microbial activity, and electro-static charge. The integrated paper can be formed using, preferably, wet laid paper-making processes for speed and efficiency.

The fiber-fiber composite has a mean pore diameter of less than or equal to about 1 micron, and preferably, less than or equal to about 0.75 micron, more preferably less than or equal to about 0.5 micron, and can be as low as 0.2 microns. The bubble point, largest pore size, of the composite is about 2.0 to about 8.0 microns, but can also be less than about 2.0 microns. The tight pore structure of the composite provides greater than about 99.95% reduction of particulates having a particle size of less than about 5 microns, while having tremendous dirt holding capacity. The fiber-fiber composite preferably has a thickness of about 0.05 to about 0.3 millimeters. The wet strength of the fiber-fiber composite is preferably about 10 to about 30% of the dry strength value, or greater than about 0.013 kg/mm.

The Fibers in the Fiber-Fiber Composite

The fiber-fiber composite of the present invention includes majority fibers and minority fibers. The minority fibers preferably provide an adhesive force that coalesces the majority fibers into the composite structure, preferably a flat sheet, paper-like structure. The adhesive force necessary to coalesce the majority fibers can be provided by heat and/or modest pressure. As the average fiber diameter decreases, the pore size of the fiber-fiber composite declines. Compression of the composite by calendaring will reduce the porosity of the composite and compress the fibers to further reduce pore size.

The Majority Fibers

One or more types of fibers may be present as the majority fibers. Majority fibers useful in making the integrated paper of the present invention are any fibers that can be fibrillated into nanofibers that have a softening point at least about 25° C. greater than that of the minority fibers such that upon heat or pressure, the majority fibers do not melt and foul the pore structure of the composite. The fibers preferably comprise organic polymeric fibers that are capable of being fibrillated. Fibrillated fibers are most preferred due to their exceptionally fine dimensions and potentially low cost. Such fibrillated fibers include, but are not limited to, polymers such as polyamide, acrylic, acrylonitrile; liquid crystal polymers such as VECTRAN® and ZYLON®, and the like; ion-exchange resins; engineered resins; cellulose; rayon; ramie; wool; silk; glass; metal; ceramic; other fibrous materials; or combinations thereof. Combinations of organic and inorganic fibers and/or whiskers whether fibrillated or not, are contemplated and within the scope of the invention. For example, glass, ceramic, or metal fibers and polymeric fibers may be used together. Glass or metal fibers can provide additional wet strength to the integrated paper. In a most preferred embodiment, fibrillated lyocell fibers are used due to their exceptionally fine dimensions and potentially low cost.

Fibrillatable cellulose fibers can be made by direct dissolution and spinning of wood pulp in an organic solvent, such as an amine oxide, and are known as lyocell fibers. Lyocell fibers have the advantage of being produced in a consistent, uniform manner, thus yielding reproducible results, which may not be the case for, for example, natural cellulose fibers. Further, the fibrils of lyocell are often curled. The curls provide a significant amount of fiber entanglement. As an added advantage, the fibrillated lyocell fibers may be produced in large quantities using equipment of modest capital cost. It will be understood that fibers other than cellulose may be fibrillated to produce extremely fine fibrils, such as for example, synthetic fibers, in particular, acrylic or polyacrylonitrile (PAN) fibers, or other cellulosic materials.

When produced by a wet laid process from fibers such as cellulose or polymer fibers, such nanofibers should have a Canadian Standard Freeness of less than or equal to about 100, preferably less than or equal to about 45, and most preferably less than or equal to about 0. However, it should be recognized that in some cases, Canadian Standard Freeness is not an ideal measure of fiber size, as in the case of extremely stiff fibers such as those produced from liquid crystal polymers such as VECTRAN®. In these cases, the fiber size should be directly assayed using microscopy. Preferably, a significant portion of the nanofibers should have an average fiber diameter less than or equal to about 1000 nanometers, more preferably less than or equal to about 400 nanometers, and nanofibers less than or equal to about 250 nanometers in diameter are most preferred.

It is preferable to chop the original fibers prior to fibrillation to a length of about 1 millimeter to about 8 millimeters, preferably about 2 millimeters to about 6 millimeters, and more preferably about 3 millimeters to about 4 millimeters, and to sustain this fiber length during the fibrillation process by avoiding excessive fiber cutting.

The Minority Fibers

The minority fibers preferably have a softening point at least 25° C. below that of the majority fibers, or of the majority fibers that have the lowest softening point. Preferably, the minority fibers are thermoset or thermoplastic materials. Fibers such as polyvinyl alcohol that dissolve at elevated temperatures in the presence of moisture are also useful as minority fibers.

The minority fibers can have average fiber diameters above and below the sub-micron range. As the fiber diameter of the minority fibers decrease, the amount of minority fibers needed to coalesce the majority fibers decrease provided that the minority fibers are well distributed amongst the majority fibers to provide the desirable degree of wet and dry strength. The pore structure of the fiber-fiber composite varies with the average fiber diameters of the majority and minority fibers. The pore structure of the composite can be further reduced when using minority fibers that shrink when heated as a result of a release of residual stress trapped within the fiber during the manufacturing process. This can pull the structure inward and make the pores smaller.

If the majority and minority fibers are similar in average fiber diameters, this leads to the highest porosity, the most uniform pore size, and the highest permeability in the resulting fiber-fiber composite. Thus, it is preferred, but not necessary, to fibrillate the minority fibers such that the minority fibers have similar Canadian Standard Freeness and dimensions as the majority fibers.

Useful minority fibers that can act as binder fibers include, but are not limited to, polyolefins, polyvinyl halides, polyvinyl esters, polyvinyl ethers, polyvinyl alcohols, polyvinyl sulfates, polyvinyl phosphates, polyvinyl amines, polyamides, polyimides, polyoxidiazoles, polytriazols, polycarbodiimides, polysulfones, polycarbonates, polyethers, polyarylene oxides, polyesters, polyarylates, phenolformaldehyde resins, melamine-formaldehyde resins, formaldehyde-ureas, ethyl-vinyl acetate copolymers, co-polymers and block interpolymers thereof, and combinations thereof. Variations of the above materials and other useful polymers include the substitution of groups such as hydroxyl, halogen, lower alkyl groups, lower alkoxy groups, monocyclic aryl groups, and the like. Other potentially applicable materials include polymers such as polystyrenes and acrylonitrile-styrene copolymers, styrene-butadiene copolymers, and other non-crystalline or amorphous polymers and structures.

Other binders that may be useful in the present invention as minority fibers if available in fiber form include endcapped polyacetals, such as poly(oxymethylene) or polyformaldehyde, poly(trichloroacetaldehyde), poly(n-valeraldehyde), poly(acetaldehyde), and poly(propionaldehyde); acrylic polymers, such as polyacrylamide, poly(acrylic acid), poly(methacrylic acid), poly(ethyl acrylate), and poly (methyl methacrylate); fluorocarbon polymers, such as poly (tetrafluoroethylene), perfluorinated ethylene-propylene copolymers, ethylene-tetrafluoroethylene copolymers, poly (chlorotrifluoroethylene), ethylene-chlorotrifluoroethylene copolymers, poly(vinylidene fluoride), and poly(vinyl fluoride); polyamides, such as poly(6-aminocaproic acid) or poly(e-caprolactam), poly(hexamethylene adipamide), poly (hexamethylene sebacamide), and poly(11-aminoundecanoic acid); polyaramides, such as poly(imino-1,3-phenyleneiminoisophthaloyl) or poly(m-phenylene isophthalamide); parylenes, such as poly-2-xylylene, and poly(chloro-1-xylylene); polyaryl ethers, such as poly(oxy-2,6-dimethyl-1,4-phenylene) or poly(p-phenylene oxide); polyaryl sulfones, such as poly(oxy-1,4-phenylenesulfonyl-1,4-phenyleneoxy-1,4-phenyl-eneisopropylide ne-1,4-phenylene), and poly(sulfonyl-1,4-phenylene-oxy-1,4-phenylenesulfonyl4,4'-biphenylene); polycarbonates, such as poly-(bisphenol A) or poly(carbonyldioxy-1,4-phenyleneisopropylidene-1,4-phenylene); polyesters, such as poly(ethylene terephthalate), poly(tetramethylene terephthalate), and poly(cyclohexyl-ene-1,4-dimethylene terephthalate) or poly(oxymethylene-1,4-cyclohexylenemethyleneoxyterephthaloyl); polyaryl sulfides, such as poly(p-phenylene sulfide) or poly(thio-1,4-phenylene); polyimides, such as poly(pyromellitimido-1,4-phenylene); polyolefins, such as polyethylene, polypropylene, poly(1-butene), poly (2-butene), poly(1-pentene), poly(2-pentene), poly(3-methyl-1-pentene), and poly(4-methyl-1-pentene); vinyl polymers, such as poly(vinyl acetate), poly(vinylidene chloride), and poly(vinyl chloride); diene polymers, such as 1,2-poly-1,3-butadiene, 1,4-poly-1,3-butadiene, polyisoprene, and polychloroprene; polystyrenes; and copolymers of the foregoing, such as acrylonitrilebutadiene-styrene (ABS) copolymers. Polyolefins that may be useful include polyethylene, linear low density polyethylene, polypropylene, poly(1-butene), poly(2-butene), poly(1-pentene), poly(2-pentene), poly(3-methyl-1-pentene), poly(4-methyl-1-pentene), and the like.

Preferred minority fibers include polyethylene, polypropylene, acrylic, polyester-polypropylene or polypropylene-polyethylene bi-component fibers, or others can be used as long as they have a softening point less than the lowest softening point of the majority fibers, and preferably at least about 25° C. lower than the lowest softening point of the majority fibers. Certain types of treated polyethylene fibers, when properly treated, as described below, are optimal, and have the additional benefit of not significantly interfering with the hydrophilic nature of the resulting fiber-fiber composite when used in modest volumes. Preferred minority fibers include FYBREL® synthetic fibers, and/or SHORT STUFF® Grades EST-8 and/or E385F, all of which are polyolefin based. FYBREL® is a polyolefin based synthetic pulp that is a highly fibrillated fiber. FYBREL® has excellent thermal moldability and provides a smooth surface to the fiber-fiber composite. SHORT STUFF® Grades EST-8 and E385F are both highly fibrillated, high density polyethylene. All of these fibers are commercially available from MiniFibers, Inc., Pittsburgh, Pa. Preferred acrylic staple fibers can be obtained from Sterling Fibers, Inc., Pace, Fla., under the trade designation RES-25; Asahi Kasei Corporation, Tokyo, Japan, under the tradename CASHMILON™; and/or Mitsubishi Rayon America, New York, N.Y., as a 3 millimeter length fibrillatable staple fiber.

Preferably, one or more types of minority fibers are present in a total amount of about 1% to about 20% by weight based on a total weight of the composite, more preferably about 4% to about 18%, and most preferably about 5% to about 15%. It is preferable that the binder material have a softening point that is significantly lower than a softening point of the majority fibers so that the composite can be heated to activate the binder fibers, while the composite does not melt and coalesce thereby losing porosity.

Methods of Making the Fiber-Fiber Composite

The fiber-fiber composite of the present invention is preferably made using wet laid processes for speed and economies of scale.

In a preferred wet laid process, a fiber tow is chopped to a specific length, usually in the range of about 1 millimeter to about 8 millimeters and in particular in the range of about 3 millimeters to about 4 millimeters. The chopped fibers are fibrillated in a device having characteristics similar to a blender, or on a large scale, in machines commonly referred to as a "hi-low", a "beater" or a "refiner". The fiber is subjected to repetitive stresses, while further chopping and the reduction of fiber length is minimized. As the fibers undergo these stresses, the fibers split as a result of weaknesses between amorphous and crystalline regions and the Canadian Standard Freeness (CSF), which is determined by a method well known in the art, begins to decline. Samples of the resulting pulp can be removed at intervals, and the CSF used as an indirect measure of the extent of fibrillation. While the CSF value is slightly responsive to fiber length, it is strongly responsive to the degree of fiber fibrillation. Thus, the CSF, which is a measure of how easily water may be removed from the pulp, is a suitable means of monitoring the degree of fiber fibrillation whenever the fibers have a good tendency to form a wet-laid sheet. However, this is not necessarily the case when handling very stiff fibers such as those made from liquid crystal polymers such as VECTRAN®. If the surface area is very high, then very little water will be drained from the pulp in a given amount of time and the CSF value will become progressively lower as the fibers fibrillate more extensively. Preferably, fibrillation occurs at temperatures greater than about 30° C. to accelerate the process. However, when fibrillating fibers such as acrylic, lower temperatures can be used to avoid softening the acrylic fibers. Enzymes may be added to further accelerate the fibrillation process.

The fibrillated fibers of a given CSF value can be directly used for producing the fiber-fiber composite or dewatered on a variety of different devices, including a dewatering press or belt, to produce a dewatered pulp. The dewatered pulp can be subsequently used to make a wet-laid fiber-fiber composite. Generally, for application in the present invention, a pulp with a CSF of below 100 is used, preferably, the CSF should be less than or equal to about 45, and more preferably less than or equal to about 0. A Canadian Standard Freeness below 0 is achieved when the fibers are fibrillated beyond the time needed to achieve a Canadian Standard Freeness of 0. The fibers can be directly sent to pulp preparation systems to create a furnish suitable for making the fiber-fiber composite.

To impart anti-microbial properties to the fiber-fiber composite, the fibrillated fibers can be treated with a microbiological interception enhancing agent. The fibers, or the fiber-fiber composite itself, can be chemically treated with any compatible microbiological interception enhancing agent known in the art, with or without a biologically active metal. Examples of suitable anti-microbial agents include, without limitation, any bactericidal agent, bacteriostatic agent, fungicidal agent, fungistatic agent, or the like, that are preferably efficacious against a broad spectrum of microbes. Specific examples of suitable bactericidal/bacteriostatic agents include, without limitation, POLYMYCIN™, BACITRACIN™, lysozyme, TRICLOSAN™, DOWCIDE™, quaternary amine salts, polyphenols, acid-anionic surfactants, amphoteric surfactant disinfectants, biguanidines, and the like. Specific examples of suitable fungicidal/fungistatic agents include, without limitation, dithiocarbamates, phthalimides, dicarboximides, organophosphates, benzimidazoles, carboxanilides, phenylamides, phosphates, and the like. A preferred microbiological interception enhancing agent is disclosed in co-pending U.S. application Ser. No. 10/286,695.

As set forth in U.S. Ser. No. 10/286,695, now U.S. Pat. No. 6,835,311, the microbiological interception enhancing agent Is set forth beginning at column 7, line 24 to column 10, line 34, again incorporated herein by reference thereto. As set forth in claim 1 of U.S. Pat. No. 6,835,311 the microbiological interception enhancing agent comprises a cationic metal complex comprising a cationic mater adsorbed on a east a portion of the microporous structure, having an associated counter ion therewith, capable of imparting a positive charge on at least a portion of said microporous structure, and where in a biologically active metal is caused to precipitate with at least a portion of the counter ion associated with the cationic material.

The fiber mixture can be directly sent to pulp preparation systems to create a furnish suitable for paper making.

Exemplary of a wet laid process includes mixing a, pulp of fibrillated lyocell fibers having a Canadian Standard Freeness of about 0, with 12% by weight EST-8 binder fibers, and about 15% by weight MICROSTRAND® 110X-475 microglass fibers to form a slurry in deionized water. A furnish is formed with about 0.5% to about 2% consistency. It is preferable to add the microbiological interception enhancing agent to the slurry, if anti-microbial properties are desired in the fiber-fiber composite as described above. Next, this pulp is partially dewatered under vacuum and rinsed with deionized water to form a wet lap. Thereafter, the fiber slurry can be directly used in the production of the fiber-fiber composite. It is preferable to send the slurry directly into a paper making machine where the economies of scale are easily achieved in making an inexpensive fiber-fiber composite for use as a flat sheet medium.

The fiber-fiber composite can also be densified during the paper-making process by passing the fiber-fiber composite through a wet press or through the use of a calendar to achieve maximum density in the final product. Heated calendaring of the composite promotes fiber-fiber bonds resulting in a densified composite with minimal tendency to shed fibers.

Exemplary Applications Of The Fiber-Fiber Composite

Many types of filtration devices and/or systems incorporating the fiber-fiber composite can be imagined. Described below are certain specific embodiments. However, these devices are exemplary and should not be construed as restricting the scope of the invention.

The fiber-fiber composite of the present invention can be used alone as flat sheet media in radial, axial or cross flow applications, and can also be used in a pleated or spiral wound configuration. The tight pore structure of the fiber-fiber composite provides a short diffusion path and, therefore, rapid diffusion kinetics of microbiological contaminants in a flowing fluid to the surface of the composite, yet retain exceptional flow with low pressure differential. The tight pore structure also provides supplemental direct mechanical interception of microbiological contaminants, greater than or equal to about 99.95% interception of particles having an average particle size of 3 to 5 microns when the mean pore size of the fiber-fiber composite is less than about 0.75 microns as determined using an Automated Capillary Flow Porometer available from Porous Materials, Inc., Ithaca, N.Y. Bacterial and viral interception can be further enhanced with treatment with any compatible anti-microbial agent. Furthermore, the fiber-fiber composite can be treated with hydrophobicity or hydrophilicity agents known in the prior art to provide the desired wetting characteristics.

When combined with other filter media, the fiber-fiber composite can be used as a prefiltration wrap around an activated carbon block filter medium. The condensed pore structure provides greater than or equal to about 99.95% interception of particles having an average particle size of 3 to 5 microns such that a carbon block that can only provide reduction in chorine, taste and odor can now provide mechanical interception of protozoan cysts such as Cryptosporidium and Giardia when used in conjunction with the fiber-fiber composite of the present invention.

The fiber-fiber composite can also be used as one or both substrates in a flat sheet medium such as PLEKX® available from KX Industries, L.P., Orange, Conn., and disclosed in U.S. Pat. No. 5,792,513, which is hereby incorporated by reference. In the PLEKX® "process", a mixture of active agents and particulate binder is laid on a substrate such as the fiber-fiber composite of the present invention. Should a water and vapor permeable top substrate be desirable, the fiber-fiber composite can be used as the top substrate of the PLEKX® material as well. The combined fiber-fiber composite PLEKX® product can be used as a flat sheet medium, pleated or spiral wound.

A particulate prefilter may be added upstream from the fiber-fiber composite to prolong the service life of the filtration system. Such particulate prefilter is known to one of skill in the art.

All configurations of the fiber-fiber composite with other types of filter media can be used in gravity or pressurize water filtration systems.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A filtration system comprising of:
an activated carbon filter medium, in combination with a high wet strength nanofiber composite having a mean pore diameter of less than about 1 µm, and a microbiological interception enhancing agent that comprises a cationic metal complex comprising a cationic material adsorbed on at least a portion of said filtration system, said cationic material having an associated counter ion therewith capable of imparting a positive charge on at least a portion of said filtration system, and wherein a biologically active metal is caused to precipitate with at least a portion of the counter ion associated with the cationic material, wherein the nanofiber composite comprises of majority fibers; and minority fibers admixed with the majority fibers wherein the minority fibers have a softening point lower than the majority fibers such that when the admixture of majority fibers and minority fibers are subjected to pressure and a temperature above the softening point of the minority fibers, the majority fibers are coalesced into said high wet strength composite.

2. A filtration system of claim 1 wherein said activated carbon filter medium comprises a carbon block having a mean pore diameter of greater than about 1 µm and wherein said filtration system can remove protozoan cysts.

3. A filtration system of claim 1 wherein said activated carbon filter medium comprises a flat sheet filter medium having immobilized therein activated carbon particles, alone or in combination with other active agents, between one or more substrates, or is admixed with fibers to result in entanglement or bonds with the fibers within said activated carbon filter medium.

4. A filtration system of claim 3 wherein said one or more substrates are made from the nanofibers composite.

5. A filtration system of claim 3 wherein said activated carbon filter medium is formed into a spiral wound or pleated flat sheet filter element.

6. A filtration system of claim 1 wherein the majority fiber of said nanofiber composite comprise glass, polymer, lyocell, cellulose, metal, ceramic, mineral, or combinations thereof.

7. A filtration system of claim 1 wherein the majority fibers of said nanofiber composite comprise lyocell.

8. A filtration system of claim 1 further including a particulate prefilter.

9. A filtration system of claim 1 wherein said nanofiber composite is a prefilter placed upstream of said activated carbon filter medium.

10. A filtration system of claim 1 wherein either or both of said activated carbon filter medium and said nanofiber composite includes said microbiological interception enhancing agent wherein said cationic material is adsorbed on at least a portion of either or both of said activated carbon filter medium and said nanofiber composite, and said associated counter ion therewith is capable of imparting a positive charge on at least a portion of either or both of said activated carbon filter medium and said nanofiber composite.

11. A filtration system of claim 1 wherein said nanofiber composite has a mean flow path of less than about 1 micron, and a bubble point equal to or less than about 8 µm.

12. A method of removing microbiological contaminants from a contaminated liquid comprising the steps of:
providing a filter medium having a microporous structure medium comprising a fiber-fiber composite having a mean pore diameter equal to or less than about 1 µm, the composite formed from a wet laid admixture of majority fibers and minority fibers, wherein the minority fibers have a softening point lower than the majority fibers such that when the admixture of majority fibers and minority fibers are subjected to a pressure and a temperature above the softening point of the minority fibers, the majority fibers and minority fibers form a paper-like structure with a porosity of greater than about 40%;
contacting the contaminated liquid with the composite which includes a microbiological interception enhancing agent comprising a cationic metal complex comprising a cationic material adsorbed on at least a portion of the microporous structure, having an associated counter ion therewith capable of imparting a positive charge on at least a portion of said microporous structure, and wherein a biologically active metal is caused to precipitate with at least a portion of the counter ion associated with the cationic material; and
removing 99.95% of contaminants having an average particle size greater than about 3 to about 5 µm.

13. A method of claim 12 wherein in the step of providing a filter medium, the filter medium further includes an activated carbon filter medium.

14. A method of claim 12 wherein in the step of providing a filter medium, the filter medium further includes an activated carbon block.

15. A method of claim 14 wherein in the step of providing a filter medium, the fiber-fiber composite is wrapped around the activated carbon block.

16. A method of claim 14 wherein in the step of providing a filter medium, the fiber-fiber composite is spirally wound and inserted within a core of the activated carbon block.

17. A method of claim 12 wherein in the step of providing a filter medium, the filter medium further includes a flat sheet medium comprising activated carbon particles immobilized on a substrate.

18. A method of claim 17 wherein in the step of providing a filter medium, the fiber-fiber composite is a substrate of the flat sheet medium.

19. A method of claim 12 wherein in the step of providing a filter medium, the filter medium further includes a particulate prefilter.

20. A method of claim 12 wherein in the step of providing a filter medium, the fiber-fiber composite is a prefilter.

21. A method of claim 12 wherein said cationic material is adsorbed on at least a portion of either or both of said majority fibers and said minority fibers.

22. A method of claim 12 wherein in the step of providing a filter medium, the fiber-fiber composite is one of pleated or spiral wound.

23. A filtration system comprising of:
an activated carbon filter medium, in combination with a high wet strength nanofiber composite having a mean pore diameter of less than about 1 µm, wherein the nanofiber composite comprises of majority fibers; and minority fibers admixed with the majority fibers, wherein the minority fibers have a softening point lower than the majority fibers such that when the admixture of majority fibers and minority fibers are subjected to pressure and a temperature above the softening point of the minority fibers, the majority fibers are coalesced into said high wet strength fiber-fiber composite, the fiber-fiber composite is treated with a microbiological interception enhancing agent which comprises a cationic metal complex comprising a cationic material adsorbed on at least a portion of the microporous structure, having an associated counter ion therewith, capable of imparting a positive charge on at least a portion of said microporous structure, and where in a biologically active metal is caused to precipitate with at least a portion of the counter ion associated with the cationic material.

24. A filtration system comprising of:
an activated carbon filter medium, in combination with a high wet strength nanofiber composite having a mean pore diameter of less than about 1 µm, wherein the nanofiber composite comprises majority fibers and minority fibers having similar average fiber diameters admixed with one another, the minority fibers having a softening point lower than the majority fibers such that when the admixture of majority fibers and minority fibers are subjected to pressure and a temperature above the softening point of the minority fibers, the majority fibers are coalesced into said high wet strength composite having a substantially uniform pore size and increased permeability due to said similar average fiber diameters of said majority and minority fibers; and
wherein either or both of said activated carbon filter medium and said nanofiber composite further includes a microbiological interception enhancing agent that comprises a cationic metal complex comprising a cationic material adsorbed on at least a portion of either or both of said activated carbon filter medium and said nanofiber composite, said cationic material having an associated counter ion therewith capable of imparting a positive charge on at least a portion of either or both of said activated carbon filter medium and said nanofiber composite, and wherein a biologically active metal is caused to precipitate with at least a portion of the counter ion associated with the cationic material.

25. A filtration system of claim 24 wherein said majority fibers comprise fibrillated majority fibers.

26. A filtration system of claim 24 wherein said minority fibers comprise fibrillated minority fibers.

27. A filtration system of claim 24 wherein both said majority fibers and said minority fibers comprise fibrillated majority fibers and fibrillated minority fibers.

28. A filtration system of claim 24 wherein said activated carbon filter medium comprises a carbon block having a mean pore diameter of greater than about 1 µm and wherein said filtration system can remove protozoan cysts.

29. A filtration system of claim 24 wherein said activated carbon filter medium comprises a flat sheet filter medium having immobilized therein activated carbon particles, alone or in combination with other active agents, between one or more substrates, or admixed with fibers to result in entanglement or bonds with the fibers within said activated carbon filter medium.

30. A filtration system of claim 24 further including a particulate prefilter.

31. A filtration system of claim 24 wherein said nanofiber composite is a prefilter placed upstream of said activated carbon filter medium.

* * * * *

UNITED STATES PATENT AND TRADEMARK OFFICE
CERTIFICATE OF CORRECTION

| | |
|---|---|
| PATENT NO. | : 7,276,166 B2 |
| APPLICATION NO. | : 10/923058 |
| DATED | : October 2, 2007 |
| INVENTOR(S) | : Evan E. Koslow |

It is certified that error appears in the above-identified patent and that said Letters Patent is hereby corrected as shown below:

Column 7, Line 55-56:

"mater adsorbed on a east" should be -- material adsorbed on at least --.

Column 8, Line 62:

"KX Industries, L.P., Orange, Conn.," should be -- KX Technologies LLC, Orange, Conn. --.

Signed and Sealed this

Eighth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,276,166 B2  Page 1 of 1
APPLICATION NO. : 10/923058
DATED : October 2, 2007
INVENTOR(S) : Evan E. Koslow It is certified that error appears in the above-identified patent and that said Letters Patent is hereby corrected as shown below:

Title Page:

"(73) Assignee: KX Industries, LP, Orange, CT (US))" should be
-- (73) Assignee: KX Technologies LLC, Orange, CT (US) --.

Signed and Sealed this

Twelfth Day of August, 2008

JON W. DUDAS
*Director of the United States Patent and Trademark Office*